US012651711B2

(12) United States Patent (10) Patent No.: US 12,651,711 B2
Boone et al. (45) Date of Patent: Jun. 9, 2026

(54) ELECTRICAL COMPONENT AND METHOD OF FORMING SAME

(71) Applicant: MEDTRONIC, INC., Minneapolis, MN (US)

(72) Inventors: Mark R. Boone, Gilbert, AZ (US); Joachim Hossick-Schott, Minneapolis, MN (US); Mark Henschel, Phoenix, AZ (US); Chunho Kim, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 468 days.

(21) Appl. No.: 18/243,274

(22) Filed: Sep. 7, 2023

(65) Prior Publication Data

US 2023/0420191 A1 Dec. 28, 2023

Related U.S. Application Data

(62) Division of application No. 17/367,831, filed on Jul. 6, 2021, now Pat. No. 11,756,741.

(60) Provisional application No. 63/058,904, filed on Jul. 30, 2020.

(51) Int. Cl.
*H01G 9/052* (2006.01)
*H01G 9/00* (2006.01)
*H01G 9/042* (2006.01)
*H01G 9/048* (2006.01)
*H01G 9/08* (2006.01)
*H01G 9/15* (2006.01)
*A61N 1/05* (2006.01)

(52) U.S. Cl.
CPC ........... *H01G 9/052* (2013.01); *H01G 9/0029* (2013.01); *H01G 9/048* (2013.01); *H01G 9/08*

(2013.01); *H01G 9/15* (2013.01); *A61N 1/05* (2013.01); *H01G 9/0425* (2013.01)

(58) Field of Classification Search
CPC ...... H01G 9/0029; H01G 9/008; H01G 9/012; H01G 9/08; H01G 9/042; H01G 9/0425; H01G 9/048; H01G 2009/05; H01G 9/052; H01G 9/055; H01G 9/07; H01G 9/15
See application file for complete search history.

(56) References Cited

U.S. PATENT DOCUMENTS

| | | | |
|---|---|---|---|
| 5,812,366 A | 9/1998 | Kuriyama | |
| 6,510,044 B1 | 1/2003 | Loeffelholz et al. | |
| 6,511,588 B1 | 1/2003 | Kobayashi | |

(Continued)

FOREIGN PATENT DOCUMENTS

JP 2000114113 4/2000

*Primary Examiner* — Scott B Geyer
(74) *Attorney, Agent, or Firm* — Mueting Raasch Group

(57) ABSTRACT

Various embodiments of an electrical component and a method of forming such component are disclosed. The electrical component includes a substrate having a first major surface, a second major surface, and a cavity disposed in the substrate. The cavity extends between the first major surface and the second major surface. The electrical component also includes an anode electrode that includes a conductive foil layer disposed on the second major surface of the substrate and over the cavity. Tantalum material is disposed within the cavity and includes tantalum particles. A dielectric layer is disposed on the tantalum particles, and an electrolyte cathode layer is disposed on the dielectric layer. The electrical component also includes a cathode electrode disposed over the cavity.

20 Claims, 3 Drawing Sheets

(56) References Cited

U.S. PATENT DOCUMENTS

| | | |
|---|---|---|
| 8,199,461 B2 | 6/2012 | Zednicek et al. |
| 8,992,635 B2 | 3/2015 | Otterstedt |
| 2003/0218859 A1 | 11/2003 | Yoshida |
| 2005/0280978 A1 | 12/2005 | Sakaguchi et al. |
| 2010/0020473 A1 | 1/2010 | Prymak et al. |
| 2012/0300369 A1 | 11/2012 | Lee et al. |
| 2016/0284476 A1 | 9/2016 | Paulus et al. |
| 2017/0069775 A1 | 3/2017 | Fenner |
| 2017/0172505 A1 | 6/2017 | Ruben et al. |
| 2018/0218859 A1 | 8/2018 | Ligtenberg et al. |
| 2018/0363158 A1 | 12/2018 | Religieux |
| 2020/0154567 A1 | 5/2020 | Kim et al. |

200

202

116
104
118

130
134
114
212

204

126

214

206

132

120
122
120
124

208

117

216

108
106
110

210

218

128

102

ELECTRICAL COMPONENT AND METHOD OF FORMING SAME

RELATED PATENT APPLICATION

This application is a divisional of U.S. application Ser. No. 17/367,831, filed Jul. 6, 2021, and which claims the benefit of U.S. Provisional Patent Application Ser. No. 63/058,904, filed on Jul. 30, 2020, which are incorporated by reference herein in their entireties.

TECHNICAL FIELD

This disclosure generally relates to electrical components. In particular, this disclosure relates to electrical components suitable for use in implantable devices.

BACKGROUND

A wide variety of electronic assemblies such as those that are utilized for implantable medical devices (IMDs) employ electronic circuitry, e.g., for providing electrical stimulation of body tissue and/or monitoring a physiologic condition. Such IMDs can deliver electrical therapy energy in the form of shocking energy and stimulating pulses to selected body tissue and typically include output circuitry for providing the electrical energy under prescribed conditions and at least one lead bearing a stimulation electrode for delivering the electrical energy to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle, and organ tissue stimulating medical devices are also known for treating a variety of conditions.

Currently available IMDs, including ICDs and implantable pulse generators (IPGs), are typically formed having a metallic housing that is hermetically sealed and, therefore, is impervious to body fluids, and a header or connector assembly mounted to the housing for making electrical and mechanical connection with one or more leads. Such devices also possess telemetry capabilities for communicating with external devices. Over the past 20 years, IMDs have evolved from relatively bulky devices to complex miniaturized devices that exhibit increasing functionality. For example, numerous improvements have been made in cardioversion/defibrillation leads and electrodes that have enabled the cardioversion/defibrillation energy to be precisely delivered to selected one or more portions of upper and lower heart chambers. The high voltage output circuitry has also been improved in many respects to provide monophasic, biphasic, or multi-phase cardioversion/defibrillation shock or pulse waveforms that are efficacious, sometimes with particular combinations of cardioversion/defibrillation electrodes.

The miniaturization of IMDs is driving size and cost reduction of all IMD components, including the electronic circuitry components, where it is desirable to increase the density and reduce the size of such components so that the overall circuitry can be more compact. As the dimensions of IMDs decrease, the electronic circuits of the IMDs are formed as integrated circuits to fit within a minimal space. Furthermore, as the dimensions of the components are also being reduced, it is desirable to improve the use of the available space within the IMD package.

Electronic circuitry for IMDs and other electronic devices can include one or more capacitors. Such capacitors are passive components that store potential energy in an electric field and are designed to add capacitance to circuits. Various types of capacitors can be utilized, including ceramic and electrolytic capacitors. Tantalum capacitors are a type of electrolytic capacitor that have a relatively high capacitance density compared to other capacitors such as ceramic capacitors.

SUMMARY

The techniques of this disclosure generally relate to electrical components and methods for forming such electrical components. In one or more embodiments, an electrical component can include tantalum material disposed within a cavity of a substrate, a cathode electrode disposed over the cavity, and an anode electrode disposed on a major surface of the substrate and over the cavity. The tantalum material can include tantalum particles. The electrical component can include a dielectric disposed on the tantalum particles and an electrolyte cathode layer disposed on the dielectric. The anode electrode can include a conductive foil layer disposed on the major surface of the substrate and over the cavity. In one or more embodiments, the electrical component can form a capacitor that can be utilized in any suitable electronic circuit or device.

In one example, aspects of this disclosure relate to an electrical component that includes a substrate having a first major surface, a second major surface, and a cavity disposed in the substrate extending between the first major surface and the second major surface. The electrical component also includes an anode electrode that includes a conductive foil layer disposed on the second major surface of the substrate and over the cavity. Tantalum material is disposed within the cavity and includes tantalum particles. A dielectric layer is disposed on the tantalum particles, and an electrolyte cathode layer is disposed on the dielectric layer. The electrical component also includes a cathode electrode is disposed over the cavity.

In another example, aspects of this disclosure relate to a method that includes providing a substrate having a first major surface and a second major surface, disposing a conductive foil layer on the second major surface of the substrate, disposing a cavity in the first major surface of the substrate, the cavity extends between the first major surface of the substrate and the conductive foil layer, disposing tantalum material in the cavity, the tantalum material comprising tantalum particles, and disposing a cathode electrode over the cavity.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The techniques of this disclosure generally relate to electrical components and methods for forming such electrical components. In one or more embodiments, the electrical component can include tantalum material including tantalum particles disposed within a cavity of a substrate, a dielectric layer disposed on the tantalum particles, an electrolyte cathode layer disposed on the dielectric layer, a cathode electrode disposed over the cavity, and an anode electrode disposed on a major surface of the substrate and over the cavity. The anode electrode can include a conductive foil layer disposed on the major surface of the substrate and over the cavity. In one or more embodiments, the electrical component can form a capacitor that can be utilized in any suitable electronic circuit or device.

In general, the present disclosure provides various embodiments of apparatuses, systems, and associated techniques that relate to electrical components. Such electrical components can include any suitable components or circuitry, e.g., capacitors, tantalum capacitors, etc. Tantalum capacitors can be desirable for their reliability and capacitance density. Because of their dimensions, tantalum capacitors are typically disposed on surfaces of integrated circuit boards. At thicknesses greater than 1 mm, typical tantalum capacitors add significantly to the size and thickness of these integrated circuit boards.

One or more embodiments of electrical components described herein can have a thickness, e.g., of no greater than 600 micrometers. Because of this decreased thickness, one or more electrical components described herein can be embedded within an integrated circuit board or integrated into a substrate, thereby enabling smaller electronic packages and assemblies.

Figure 1:
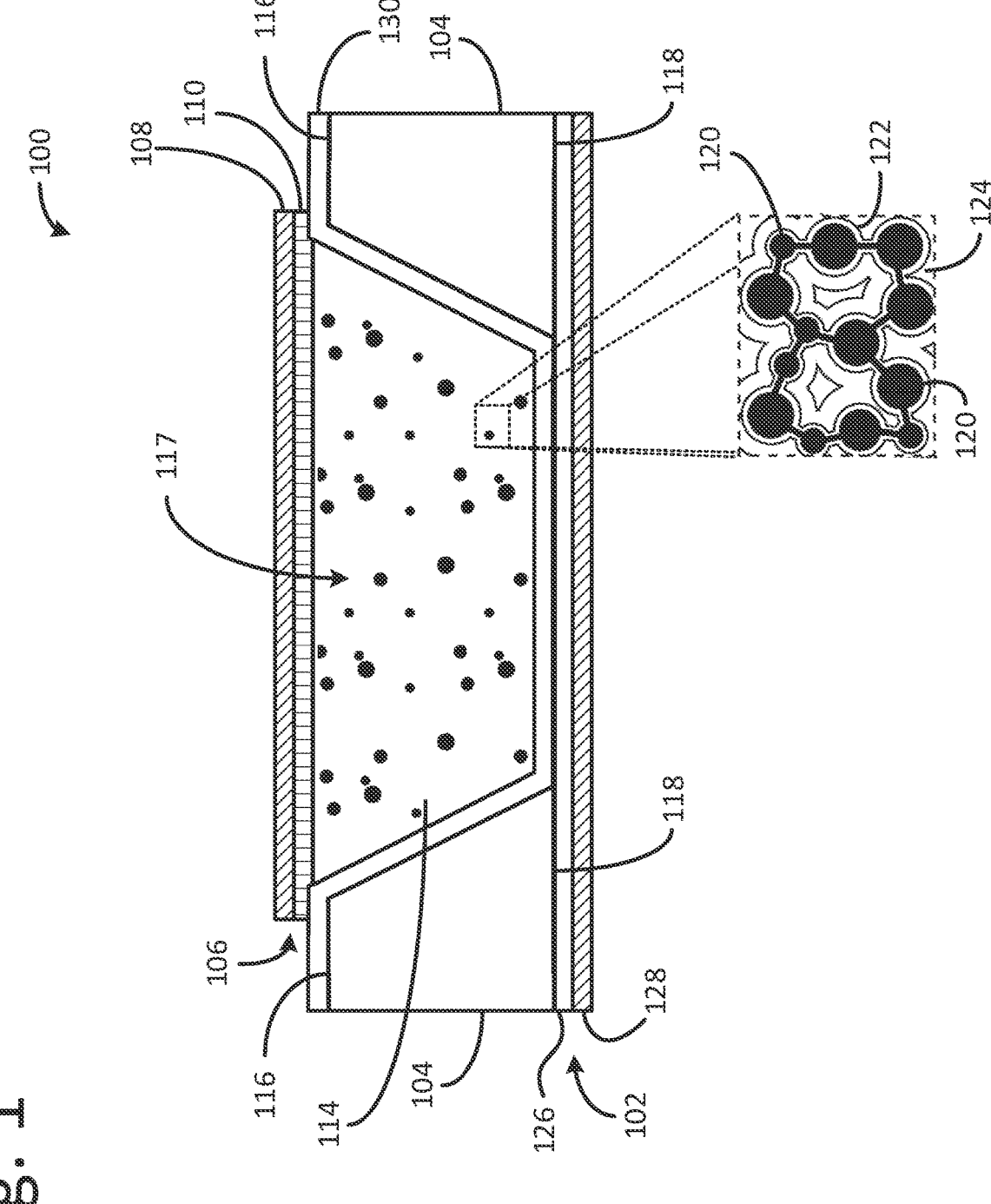
FIG. 1 is a schematic cross-section view of one embodiment of an electrical component.

FIG. 1 is a schematic cross-section view of one embodiment of an electrical component 100. Electrical component 100 includes a substrate 104 having a first major surface 116, a second major surface 118, and a cavity 117 disposed in the substrate and extending between the first major surface 116 and the second major surface 118. The electrical component 100 also includes an anode electrode 102 including a conductive foil layer 126 disposed on the second major surface 118 of the substrate 104 and over the cavity 117. The electrical component 100 also includes tantalum material 114 disposed within the cavity 117, where the tantalum material includes tantalum particles 120. Further, the electrical component 100 includes a dielectric layer 122 disposed on the tantalum particles 120, an electrolyte cathode layer 124 disposed on the dielectric layer 122, and a cathode electrode 106 disposed over the cavity 117.

The electrical component 100 can be utilized in any suitable device or electrical circuitry, e.g., printed circuit boards, integrated circuit packages, substrates, glass substrates, ceramic substrates, sapphire substrates, silicon substrates, etc. Further, the electrical component 100 can exhibit any suitable characteristics. For example, the electrical component 100 can include any suitable amount of tantalum by volume of the electrical component. Further, the electrical component 100 can have any suitable dimensions. In one or more embodiments, the electrical component 100 can have a height or thickness as measured in a direction orthogonal to the first and second major surfaces 116, 118 of the substrate 104 of no greater than 500 micrometers.

The substrate 104 can include any suitable material or materials, e.g., silicon, N-type silicon, sapphire, glass, ceramic, alumina, etc. In one or more embodiments, the substrate 104 is silicon. The substrate 104 can include any suitable dimensions and take any suitable shape. In one or more embodiments, the substrate 104 may have a height or thickness extending between the first major surface 116 and the second major surface 118 of at least 50 micrometers and no greater than 300 micrometers. In one or more embodiments, the thickness of the substrate 104 extending between the first major surface 116 and the second major surface 118 may be no greater than 500 micrometers. For example, the thickness of the substrate 104 may be equal to or less than 500 micrometers, equal to or less than 450 micrometers, equal to or less than 400 micrometers, equal to or less than 450 micrometers, equal to or less than 400 micrometers, equal to or less than 350 micrometers, equal to or less than 300 micrometers, equal to or less than 250 micrometers, equal to or less than 200 micrometers, equal to or less than 150 micrometers, or equal to or less than 100 micrometers.

The cavity 117 is disposed in the substrate 104 and extends between the first major surface 116 and the second major surface 118 of the substrate. The cavity 117 can include any suitable dimensions and take any suitable shape or shapes. Further, the cavity 117 can be disposed in the substrate 104 using any suitable technique or techniques, e.g., wet etching, dry etching, mechanical etching, laser etching, etc. Although illustrated as including one cavity 117, the electrical component 100 can include any suitable number of cavities.

Disposed within the cavity 117 is the tantalum material 114, which fills at least a portion of the cavity. In one or more embodiments, the size and shape of the tantalum material 114 is determined by the size and shape of cavity 117. Tantalum material 114 includes tantalum particles 120. The tantalum particles 120 may be bonded tantalum particles. Any suitable tantalum particles 120 can be utilized in the tantalum material 114. Further, the tantalum particles 120 can have any suitable dimensions. The tantalum particles 120 can be electrically and mechanically coupled together or bonded using any suitable technique or techniques. In one or more embodiments, the tantalum particles 120 can be sintered together using any suitable technique or techniques, e.g., heating, laser, microwave, spark plasma, etc. Further, the tantalum material 114 can be disposed within the cavity 117 using any suitable technique or techniques, e.g., deposition, printing, stencil printing, dispensing, jetting, etc. In one or more embodiments, the tantalum material 114 can include tantalum paste. Such tantalum paste can include any suitable binding agents, e.g., organic binders, solvents, etc.

The tantalum material 114 can further include a dielectric layer 122 disposed on a surface of one or more of the tantalum particles 120. In one or more embodiments, the dielectric layer 122 can be disposed on surfaces of substantially all of the tantalum particles 120. The dielectric layer 122 can include any suitable dielectric material or materials, e.g., tantalum pentoxide (Ta2O5). Further, the dielectric layer 122 can be formed using any suitable technique or techniques, e.g., anodization, wet-forming, atomic layer deposition, annealing, etc.

Further, the tantalum material 114 can also include an electrolyte cathode layer 124 disposed on the dielectric layer 122. The electrolyte cathode layer 124 can include any suitable material or materials, e.g., manganese dioxide, conductive polymer, etc. Further, the electrolyte cathode layer 124 can include any suitable dimensions and take any suitable shape or shapes. The electrolyte cathode layer 124 can be formed using any suitable technique or techniques, e.g., pyrolysis, impregnation, printing.

The electrical component 100 can also include the anode electrode 102, which is disposed on the second major surface 118 of the substrate 104 and over the cavity 117. The anode electrode 102 can include any suitable electrically conductive material or materials, e.g., copper, gold, silver, tantalum, graphite, aluminum, chrome, carbon, etc. The anode electrode 102 can include any suitable dimensions and take any suitable shape or shapes. Further, the anode electrode 102 can be formed using any suitable technique or techniques, e.g., deposition, chemical vapor deposition (CVD), physical vapor deposition (PVD), sputtering, electroplating, printing, dispensing, sintering, lasering, pressing, etc.

The anode electrode 102 can include one or more layers. In one or more embodiments, the anode electrode 102 can include a conductive foil layer 126 disposed on the second major surface 118 of the substrate 104 and over the cavity 117. The conductive foil layer 126 can include any suitable dimensions and take any suitable shape or shapes. The conductive foil layer 126 can include any suitable material or materials, e.g., tantalum, titanium, doped silicon, or other conductive material. In one or more embodiments, the conductive foil layer 126 is a tantalum foil layer. The conductive foil layer 126 can be formed using any suitable technique or techniques, e.g., pressing, sintering, lasering, etc. The conductive foil layer 126 can have a thickness in a range of at least 10 micrometers and no greater than 25 micrometers.

In one or more embodiments, the anode electrode 102 can also include an anode conductor layer 128 disposed on the conductive foil layer 126. The anode conductor layer 128 can also include any suitable dimensions and take any suitable shape or shapes. The anode conductor layer 128 can be formed using any suitable technique or techniques, e.g., deposition, PVD, CVD, sputtering, electroplating, foil lamination, etc. The anode conductor layer 128 can include any suitable electrically conductive material or materials, e.g., copper, gold, silver, aluminum, or other conductive material.

In one or more embodiments, a tantalum layer 130 can be disposed between the tantalum material 114 and the anode electrode 102. The tantalum layer 130 can be disposed using any suitable technique or techniques, e.g., deposition, chemical vapor deposition, physical vapor deposition, sputtering, electroplating, printing, dispensing, etc. In one or more embodiments, the tantalum layer 130 has a thickness of at least 1 micrometer and no greater than 2 micrometers. In one or more embodiments, the tantalum layer 130 can be sintered to the tantalum particles 120 and the conductive foil layer 126. In one or more embodiments, the tantalum layer 130 can further be disposed on surfaces of the cavity 117 and the first major surface 116 of the substrate 104. The tantalum layer 130 can have a thickness of at least 500 nanometers and no greater than 2 micrometers.

Disposed on the tantalum layer 130 and over the cavity 117 of the substrate 104 is the cathode electrode 106. The cathode electrode 106 can include any suitable dimensions and take any suitable shape or shapes. The cathode electrode 106 can include any suitable electrically conductive material or materials, e.g., the same electrically conductive materials described herein regarding the anode electrode 102. Further, the cathode electrode 106 can include any suitable number of layers. The cathode electrode 106 can be formed using any suitable technique, e.g., the same technique or techniques described herein regarding the anode electrode 102.

In one or more embodiments, the cathode electrode 106 can include a cathode connection layer 110 disposed on the tantalum layer 130 and over the cavity 117 of the substrate 104. The cathode connection layer 110 can include any suitable electrically conductive material or materials, e.g., the same electrically conductive materials described herein regarding the anode electrode 102. Further, the cathode connection layer 110 can include any suitable dimensions and take any suitable shape or shapes. The cathode connection layer 110 can be formed using any suitable technique or techniques, e.g., the same technique or techniques described herein regarding the anode electrode 102.

In one or more embodiments, the cathode electrode 106 can include a cathode conductor layer 108 disposed on the cathode connection layer 110. The cathode conductor layer 108 can include any suitable electrically conductive material or materials, e.g., the same electrically conductive materials described herein regarding the anode electrode 102. Further, the cathode conductor layer 108 can include any suitable dimensions and take any suitable shape. The cathode conductor layer 108 can be formed using any suitable technique or techniques, e.g., the same technique or techniques described herein regarding the anode electrode 102. In one or more embodiments, the cathode conductor layer 108 can be patterned using any suitable technique or techniques to provide a patterned conductive layer.

Figure 2:
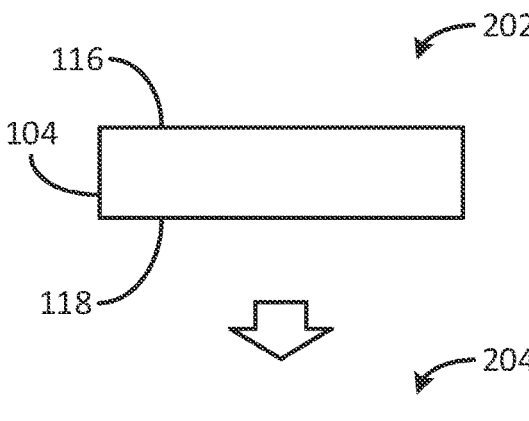
FIG. 2 is a schematic flow diagram of a process for forming the electrical component of FIG. 1.
Figure 2:
Figure 2:
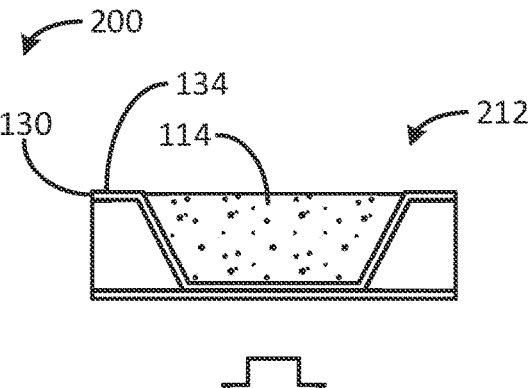
Figure 2:
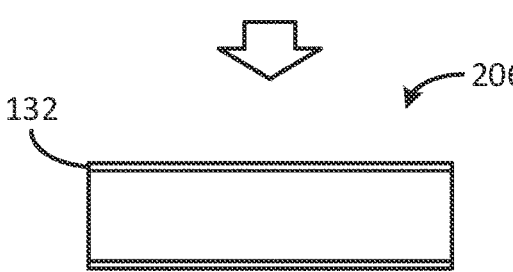
Figure 2:
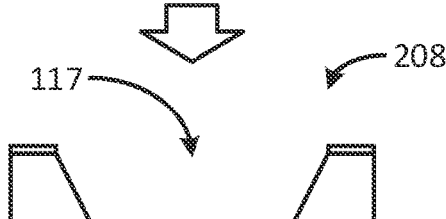
Figure 2:
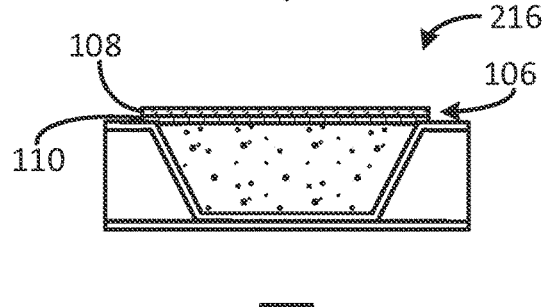
Figure 2:
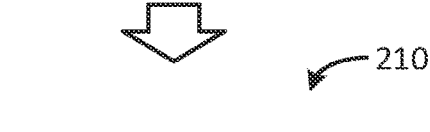
Figure 2:
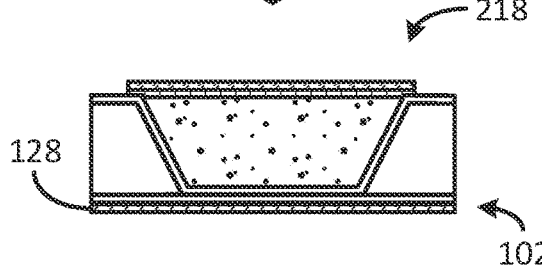

The electrical component 100 can be manufactured utilizing any suitable technique or techniques. For example, FIG. 2 is a schematic flow diagram of one embodiment of a method 200 of forming a plurality of electrical components 100. Although described in reference to electrical component 100 of FIG. 1, the method 200 can be utilized to form any suitable electrical component.

At 202, the substrate 104 is provided. The substrate 104 includes the first major surface 116 and the second major surface 118.

At 204, the conductive foil layer 126 can be disposed on the second major surface 118 of the substrate 104 using any suitable technique or techniques, e.g., sintering, pressing, lasering, diffusion bonding, etc. In one or more embodiments, the conductive foil layer 126 can be pressed or flattened to the second major surface 118 of the substrate 104 while sintering or diffusion bonding the conductive foil layer to the substrate to form the conductive foil layer 126.

At 206, a field oxide hard mask 132 can be disposed on the first major surface 116 of the substrate 104. The field oxide hard mask 132 may be disposed using any suitable technique or techniques, e.g., growing, deposition, sputtering, etc. At 208, one or more portions of the field oxide hard mask 132 may be removed and one or more cavities 117 can be disposed in the first major surface 116 of the substrate 104. The one or more portions of the field oxide hard mask 132 may be removed using any suitable technique or techniques, e.g., etching, lasering, etc. The one or more cavities 117 can be disposed in the first major surface 116 of the substrate 104 using any suitable technique or techniques, e.g., anisotropic-etching, wet-etching, lasering, sawing, etc. In one or more embodiments, the one or more cavities 117 may be formed using anisotropic-etching. The one or more cavities 117 may extend between the first major surface 116 and the second major surface 118 of the substrate 104. The conductive foil layer 126 may be exposed through the one or more cavities 117. At 210, the field oxide hard mask 132 can be removed from the substrate 104 using any suitable technique or techniques, e.g., wet etching, dry etching, lasering, etc.

At 212, the tantalum layer 130 can be disposed on surfaces of the one or more cavities 117 and the tantalum material 114 can be disposed in the one or more cavities. The tantalum layer 130 can be disposed on surfaces of the one or more cavities 117 using any suitable technique or techniques, e.g., deposition, PVD, CVD, sputtering, electroplating, foil lamination, etc. In one or more embodiments, the tantalum layer 130 is disposed with a thickness of at least 1 micrometer and no greater than 2 micrometers. Furthermore, an oxide layer 134 can be disposed on the tantalum layer 130 using any suitable technique or techniques, at 212. In one or more embodiments, the oxide layer 134 may be disposed by growing the oxide layer in a diffusion furnace containing water vapor (e.g., wet oxide growth) at a temperature between 1000 degrees Celsius and 1200 degrees Celsius. In one or more embodiments, the oxide layer 134 may be disposed by placing the substrate 104 in an oxygen rich environment and heating the substrate and the tantalum layer 130. The substrate 104 and tantalum layer 130 may be heated to at least 500 degrees Celsius for at least 10 minutes. Subsequent to the oxide layer 134 being disposed, the substrate 104, the tantalum layer 130, and the oxide layer 134 may be annealed to drive the oxide layer into the tantalum layer. Annealing may include heating to at least 600 degrees Celsius for at least 10 minutes.

At 212, the tantalum material 114 including the tantalum particles 120 can be disposed into the one or more cavities 117 of the substrate 104 using any suitable technique or techniques, e.g., printing, pressing, placing, etc. The tantalum material 114 may include, e.g., tantalum powder, a tantalum slug, tantalum paste, etc. In embodiments where the tantalum material 117 includes tantalum paste, the tantalum paste can be dried and debindered using any suitable technique or techniques at 212, for example, heating the tantalum paste.

In one or more embodiments, the tantalum material 114 can be sintered at 212 using any suitable technique or techniques. Sintering the tantalum material 114 can cause the tantalum particles 120 to at least partially fuse together to form one or more mechanical and electrical connections between the tantalum particles. Additionally, sintering can cause one or more of the tantalum particles 114 to fuse to the tantalum layer 130, forming at least one mechanical and electrical connection between the tantalum material and the tantalum layer. In one or more embodiments, the tantalum material 114 can be sintered by heating the material to a temperature of at least 1200 degrees Celsius and no greater than 3000 degrees Celsius.

At 214, the dielectric layer 122 can be disposed on the tantalum particles 120 using any suitable technique or techniques. In one or more embodiments, the dielectric layer 122 may be disposed using, e.g., anodization, wet-forming, atomic layer deposition, annealing, etc.

Further, at 214, the electrolyte cathode layer 124 can be disposed on the dielectric layer 122 using any suitable technique or techniques. In one or more embodiments, the electrolyte cathode layer 124 may be disposed using, e.g., pyrolysis, impregnation, printing, dispensing, dip-coating, etc.

At 216, the cathode electrode 106 can be disposed over the one or more cavities 117 using any suitable technique or techniques, e.g., deposition, PVD, CVD, sputtering, electroplating, foil lamination, etc. In one or more embodiments, the cathode electrode 106 may be disposed on the electrolyte cathode layer 124 and the tantalum layer 130. Disposing the cathode electrode 106 can include disposing one or more layers. For example, in one or more embodiments, disposing the cathode electrode 106 can include disposing the cathode connection layer 110 and the cathode conductor layer 108. The cathode connection layer 110 can be disposed over the one or more cavities 117 using any suitable technique or techniques, e.g., deposition, PVD, CVD, sputtering, electroplating, foil lamination, etc. The cathode conductor layer 108 can be disposed on the cathode connection layer 110 using any suitable technique or techniques, e.g., deposition, PVD, CVD, sputtering, electroplating, foil lamination, shadow masking, etc.

At 218, the anode conductor layer 128 can be disposed on the conductive foil layer 126 using any suitable technique or techniques, e.g., deposition, chemical vapor deposition (CVD), physical vapor deposition (PVD), sputtering, electroplating, printing, dispensing, etc.

Figure 3:
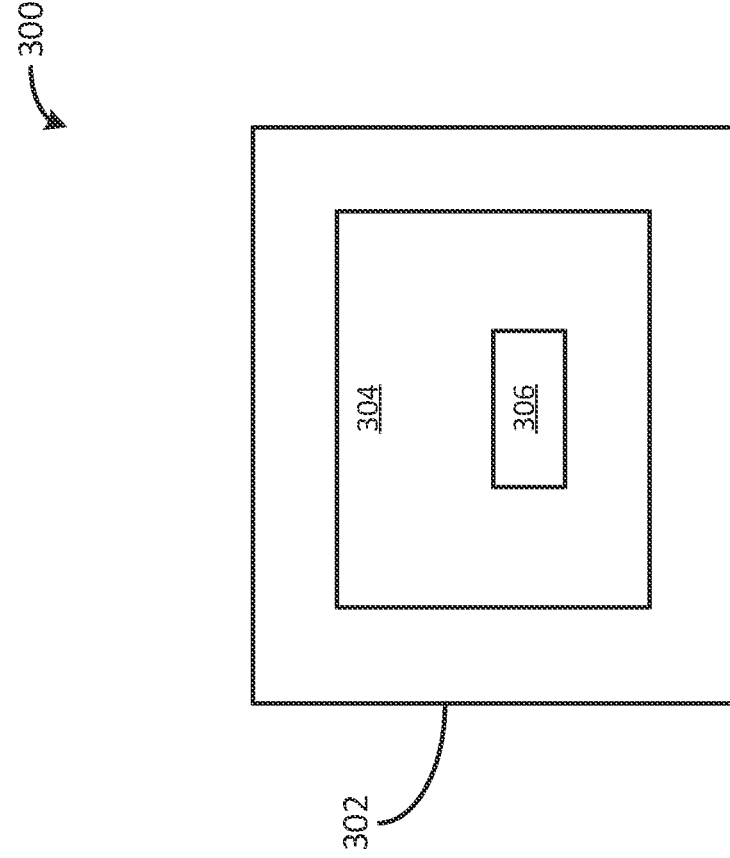
FIG. 3 is a schematic diagram of an implantable medical device including the electrical component of FIG. 1.

The electrical component 100 as described herein can be utilized with any suitable implantable medical devices. For example, FIG. 3 is a schematic diagram of an implantable medical device 300. Implantable medical device 300 includes a housing 302 and a circuit electronic assembly 304 within the housing. The electronic assembly 304 can include an electrical component 306. The electrical component 306 can include any suitable electrical component, e.g., the electrical component 100 of FIG. 1.

The implantable medical device 300 can include any suitable medical device. In one or more embodiments, the implantable medical device 300 can include an implantable defibrillator, pacemaker, neurostimulator, etc.

It should be understood that various aspects disclosed herein can be combined in different combinations than the combinations specifically presented in the description and accompanying drawings. It should also be understood that, depending on the example, certain acts or events of any of the processes or methods described herein can be performed in a different sequence, can be added, merged, or left out altogether (e.g., all described acts or events can not be necessary to carry out the techniques). In addition, while certain aspects of this disclosure are described as being performed by a single module or unit for purposes of clarity, it should be understood that the techniques of this disclosure can be performed by a combination of units or modules associated with, for example, a medical device.

In one or more examples, the described techniques can be implemented in hardware, software, firmware, or any combination thereof. If implemented in software, the functions can be stored as one or more instructions or code on a computer-readable medium and executed by a hardware-based processing unit. Computer-readable media can include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions can be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein can refer to any of the foregoing structure or any other physical structure suitable for implementation of the described techniques. Also, the techniques could be fully implemented in one or more circuits or logic elements.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method comprising:
   providing a substrate comprising a first major surface and a second major surface;
   disposing a conductive foil layer on the second major surface of the substrate;
   disposing a cavity in the first major surface of the substrate, wherein the cavity extends between the first major surface of the substrate and the conductive foil layer;
   disposing tantalum material in the cavity, the tantalum material comprising tantalum particles; and
   disposing a cathode electrode over the cavity.

2. The method of claim 1, further comprising:
   disposing a field oxide layer on surfaces of the cavity prior to disposing tantalum material in the cavity; and
   annealing the substrate and the field oxide layer prior to disposing tantalum material in the cavity.

3. The method of claim 1, further comprising:
   disposing a tantalum layer on surfaces of the cavity prior to disposing tantalum material in the cavity; and
   annealing the substrate and the tantalum layer prior to disposing tantalum material in the cavity.

4. The method of claim 1, further comprising sintering the tantalum particles prior to disposing the cathode electrode.

5. The method of claim 4, wherein sintering the tantalum particles comprises fusing one or more of the tantalum particles to the tantalum layer.

6. The method of claim 4, wherein sintering the tantalum particles comprises heating the tantalum particles to a temperature of at least 1200 degrees Celsius and no greater than 3000 degrees Celsius.

7. The method of claim 1, wherein disposing the cavity in the first major surface of the substrate comprises wet-etching the substrate to form the cavity.

8. The method of claim 1, further comprising:
   disposing a dielectric layer on surfaces of the tantalum particles prior to disposing the cathode electrode; and
   disposing an electrolyte cathode layer in spaces between the tantalum particles prior to disposing the cathode electrode.

9. The method of claim 8, wherein disposing the electrolyte cathode layer comprises disposing a conductive polymer in vacuum conditions.

10. The method of claim 8, wherein disposing the dielectric layer comprises anodizing the tantalum particles to form the dielectric layer.

11. The method of claim 1, further comprising disposing an anode conductor layer on the conductive foil layer.

12. The method of claim 1, wherein disposing the conductive foil layer comprises sintering the conductive foil layer to the second major surface of the substrate.

13. The method of claim 12, wherein disposing the conductive foil layer further comprises flattening the conductive foil layer against the substrate while diffusion bonding the conductive foil layer to the substrate.

14. The method of claim 1, wherein disposing the cathode electrode comprises:
   disposing a cathode connection layer over the cavity; and
   disposing a cathode conductor layer on the cathode connection layer.

15. The method of claim 1, further comprising:
   disposing a field oxide hard mask on the first major surface of the substrate prior to disposing the cavity in the first major surface of the substrate; and
   removing one or more portions of the field oxide hard mask when disposing the cavity in the first major surface of the substrate.

16. The method of claim 1, further comprising:
   disposing a tantalum layer on surfaces of the cavity prior to disposing tantalum material in the cavity; and
   disposing a field oxide layer on the tantalum layer prior to disposing tantalum material in the cavity.

17. The method of claim 16, wherein disposing the field oxide layer comprises:
   placing the substrate in an oxygen rich environment; and
   heating the substrate and the tantalum layer.

18. The method of claim 17, further comprising annealing the substrate, the tantalum layer, and the field oxide layer prior to disposing the tantalum material in the cavity.

19. The method of claim 1, wherein disposing the cavity in the first major surface of the substrate comprises anisotropic-etching the substrate to form the cavity.

20. The method of claim 1, wherein disposing the tantalum material comprises printing the tantalum into the cavity.

* * * * *